United States Patent [19]

Kirchner

[11] Patent Number: 4,671,259

[45] Date of Patent: Jun. 9, 1987

[54] JET TIP FOR AN ORAL HYGIENE APPLIANCE WITH A SINGLE OR MULTIPLE STREAM

[75] Inventor: Horst Kirchner, Eschborn, Fed. Rep. of Germany

[73] Assignee: Braun Aktiengesellschaft, Kronberg, Fed. Rep. of Germany

[21] Appl. No.: 759,945

[22] Filed: Jul. 29, 1985

[30] Foreign Application Priority Data

Aug. 13, 1984 [DE] Fed. Rep. of Germany ....... 3429737
Aug. 13, 1984 [DE] Fed. Rep. of Germany ... 8423982[U]

[51] Int. Cl.$^4$ .................... A61H 9/00; A61G 17/02
[52] U.S. Cl. ........................................ 128/66; 433/80
[58] Field of Search ............... 433/80, 88; 128/66; 239/460, 440, 441; 222/486

[56] References Cited

U.S. PATENT DOCUMENTS

| | | | |
|---|---|---|---|
| 2,550,565 | 4/1951 | Hyser | 433/88 |
| 3,227,158 | 1/1966 | Mattingly | 128/66 |
| 3,739,983 | 6/1973 | Jousson | 128/66 |
| 4,079,762 | 3/1978 | Hanson | 239/460 |
| 4,129,257 | 12/1978 | Eggert | 239/460 |

FOREIGN PATENT DOCUMENTS

| | | | |
|---|---|---|---|
| 1174878 | 9/1984 | Canada | 128/66 |
| 2050687 | 4/1978 | Fed. Rep. of Germany | 128/66 |
| 2930132 | 2/1980 | Fed. Rep. of Germany | 239/460 |
| 2200083 | 4/1981 | Fed. Rep. of Germany | 128/66 |
| 335799 | 3/1959 | Switzerland | 128/66 |
| 982598 | 2/1965 | United Kingdom | 239/460 |

*Primary Examiner*—John J. Wilson

[57] ABSTRACT

The invention relates to a jet tip on the handle of an oral hygiene appliance. The jet of the jet tip has an opening in which a slidable core piece is displaceable, which core piece exposes only the output openings for a multiple stream in one of its two extreme positions in the jet and only a single output opening for a single stream in its other extreme position. Advantageously, when the core piece moves from one extreme position to the other, contaminants or calcium deposits are automatically and mechanically removed from the outlet opening or outlet openings which is or are not exposed. The core piece can be positively mounted in the jet and be movable by pressure or tension force exerted by a spring and be thereby automatically locked into its two extreme positions.

16 Claims, 8 Drawing Figures

JET TIP FOR AN ORAL HYGIENE APPLIANCE WITH A SINGLE OR MULTIPLE STREAM

The invention relates to a jet tip mounted on the handle of a oral hygiene appliance for producing one or more streams of liquid.

Jet tips of this type have been known for a long time, for example from U.S. Pat. No. 3,227,158, in which the jet tip is provided with only one opening. Subsequent investigations into the medical effectiveness of oral hygiene appliances led among other things to the finding (see for example German Pat. No. 20 50 687) that a single stream of liquid expelled at a relatively high pressure may have negative effects on the health of the gum. For this reason, as is already known from Swiss Pat. No. 335 799, a jet tip with several outlet openings is viewed as being more advantageous for gum massage.

For cleaning the spaces between the teeth, however, it is more advantageous to use a single-stream jet tip, as before. In order not always to have to replace the jet tip which has just been inserted into the handle, or to have to replace the handle itself for the two different applications of the oral hygiene appliance—gum massage or cleaning the spaces between the teeth, German Pat. No. 30 44 025 A1 proposed fitting the handle with a jet which has a jet tip arrangement, which can discharge either a single stream or a plurality of streams as a so-called combination jet. For this reason, the base of the handle was provided with two parallel liquid channels disposed in a lengthwise-displaceable insert, one of which channels can be connected to the liquid inlet by means of a slide switch, whereby the shaft mountable on the handle has two different kinds of jet tips on its upper end as well as two parallel channel connected with the liquid channels located in the handle, whereby one channel ends in a single-stream and the other channel in a multiple-stream jet.

The combination nozzle according to German Pat. No. 30 44 025 A1 has the following drawbacks:

(a) Because of the two liquid channels that must be made to run side by side lengthwise, manufacture is more expensive and the shaft is thicker and hence more awkward.

(b) It involves additional sealing and a considerable increase in manufacturing costs together with drawback (a) above.

(c) The two jet tips located together at the upper end of the shaft require a jet with a relatively large surface area, making orientation of the stream difficult.

The jet tip known from German Pat. No. 20 50 687 has outlet openings in its jet which have diameters of about 0.1 mm to 0.5 mm, so that they can easily be clogged by contaminants or calcium deposits. Such contaminants are usually troublesome to remove, for example by compressed air or a suitably thin needle.

To facilitate cleaning of the outlet openings in the jet, according to German Pat. No. 22 00 083 C3, an axially displaceable insert is provided in an opening in the jet, which insert, when the jet tip is in the so-called spray position, is pressed in sealing fashion against the border of the opening by the liquid pressure prevailing in the jet and allows liquid to flow out only through a few grooves provided in the border. If the jet is not being used, the insert can easily be brought to the so-called inner position, in which the grooves provided in the border of the opening can be revealed and are hence easier to clean.

A disadvantage of this known jet consists in the fact that, at least in the case of stubborn contaminants or calcium deposits, each individual groove must be cleaned separately by hand with an appropriate object.

Accordingly, the goal of the invention is to provide a jet for the jet tip of an oral hygiene appliance which does not exhibit the aforementioned disadvantages of known designs and all of the outlet openings of which can be reliably cleaned by very simple measures without using additional tools.

Embodiments of the invention are described in greater detail with reference to FIGS. 1 to 8 below which show:

Figure 5:
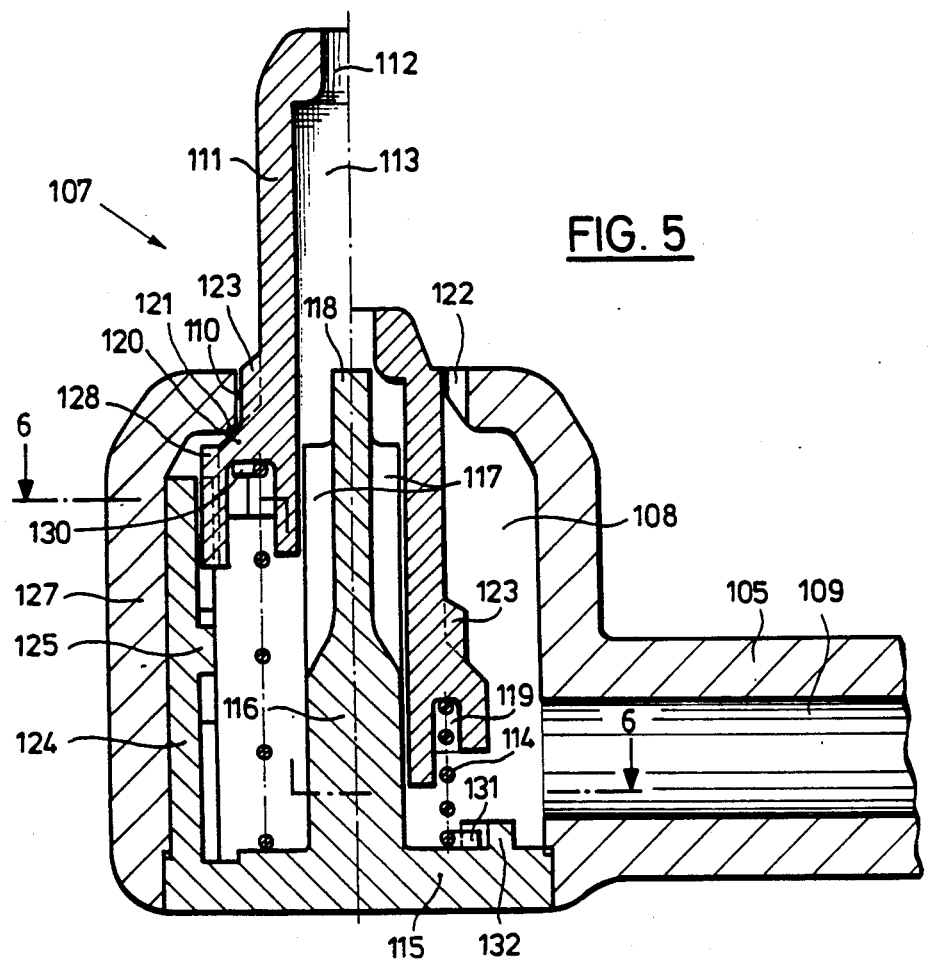
Figure 6:
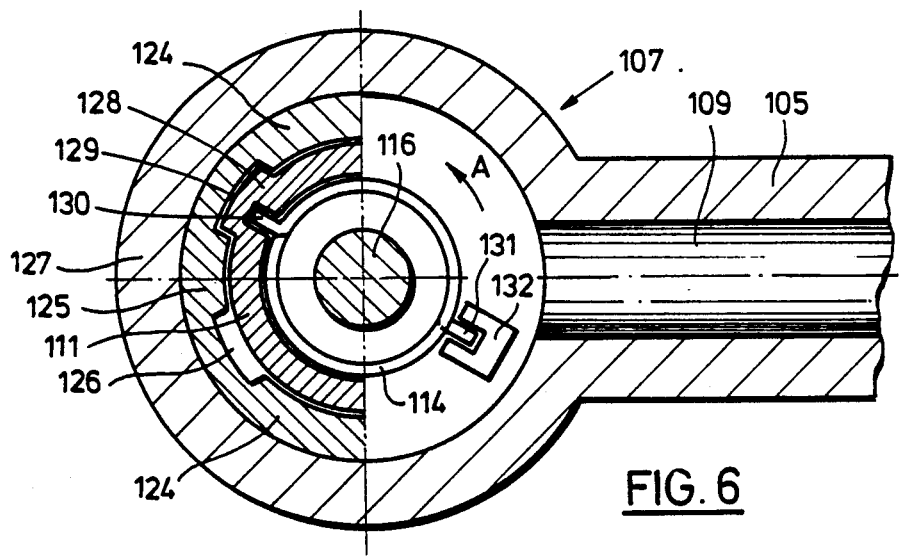

FIG. 5 is a lengthwise section through a third embodiment of a jet, whereby the core piece is in its first extreme position in the right part of the figure and the jet emits a multiple stream, while the core piece is in its second extreme position in the left part of this figure, in which the jet emits only a single stream, FIG. 6 is a section along line 6—6 in FIG. 5, whereby, in the left part of this figure, the core piece and the coil spring are shown rotated by 30° around their common axis opposite the direction of arrow A.

Figure 8:
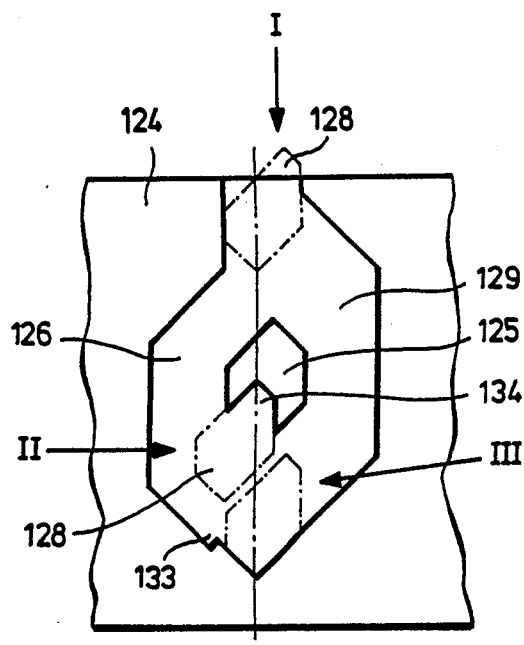
Figure 7:
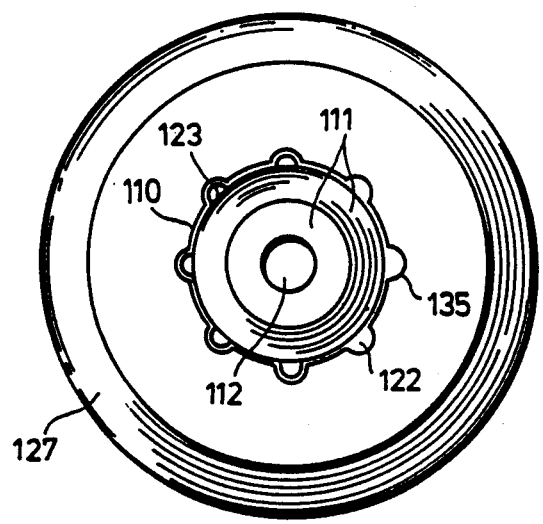

FIG. 7 is a top view of the jet of FIG. 5,

FIG. 8 is a schematic representation of the device which causes the core piece after each depression to shift from one extreme position to the other.

Figure 1:
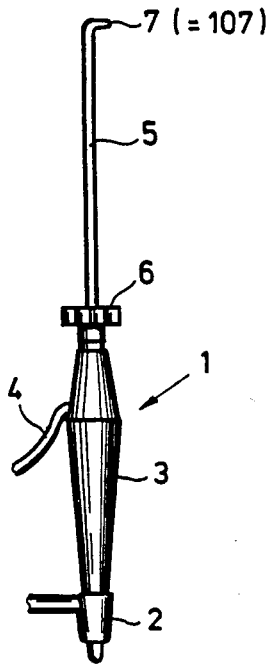
FIG. 1 is a schematic representation of the handle of an oral hygiene appliance.

FIG. 1 shows a handle 1 of an oral hygiene appliance not shown here, operated by an electric pump or only by the pressure of the water line, which handle is inserted into a holder 2 attached to the oral hygiene appliance. Handle 1 consists essentially of a base 3, in which a liquid line 4 connected to the oral hygiene appliance terminates, and of a shaft 5 interchangeably mounted in base 3 which shaft 5 connected in sealing fashion by means of a knurled knob 6 with base 3. Liquid flows pulsewise or continuously from the drive part of the oral hygiene appliance into base 3 and thence into shaft 5, which has a jet tip at its free end with a jet 7, from which a multiple stream or optionally a single stream or multiple stream emerges.

Figure 2:
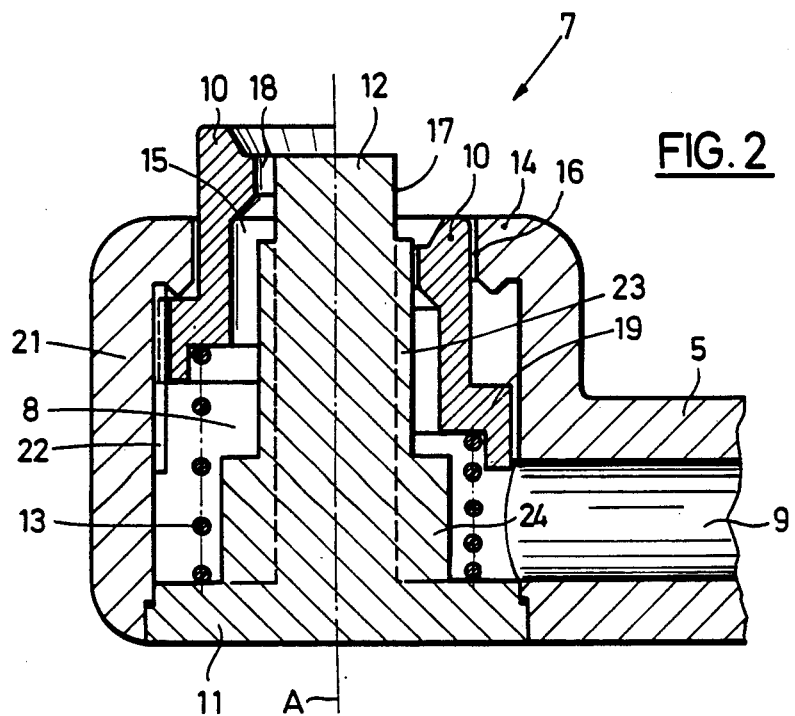
FIG. 2 is a lengthwise section through a first embodiment of a multiple-stream tip, whereby the insert is in the spray position on the left side of the figure and in the cleaning position on the right side of the figure.
Figure 3:
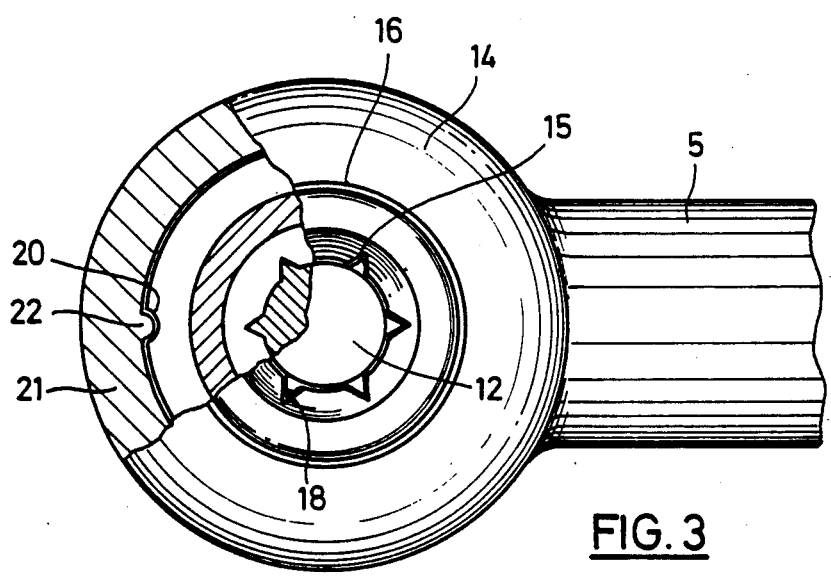
FIG. 3 is a partially cut-away top view of the jet in FIG. 2.

According to FIGS. 2 and 3, jet 7 consists essentially of a cylindrical liquid chamber 8, which is supplied by line 9 passing through shaft 5, a movable, rotationally symmetric insert 10, and a cylindrical core piece 12 formed on the rear wall 11 of liquid chamber 8 and extending into the interior thereof. Insert 10 can be depressed against the force exerted by a coil spring 13 from the position shown on the left of FIG. 2 into the position on the right in FIG. 2 vertically in an opening 15 in the front wall 14 of jet 7. The circular opening 15 is formed on the one hand from the inside jacket surface of pierced front wall 14 of jet 7 which represents its outer limit 16 and on the other hand from the outer jacket surface of core piece 12 which represents its inner limit 17, whereby the core piece serves simultaneously as a guide for insert 10. Insert 10 has six triangular grooves 18 on its inner circumference, from which grooves the liquid flowing via line 9 into liquid chamber 8 exits streamwise, provided insert 10 is in the position shown on the left in FIG. 2 (spray position).

Insert 10 is formed as an undercut hollow cylinder 19 at its lower part, which cylinder has a groove 20 at its outer jacket surface into which groove protrudes a nose 22 formed on the inner side of left side wall 21 of jet 7, which nose secures insert 10 against rotation around its axis A. The undercutting of hollow cylinder 19 produces one of the two supporting surfaces of coil spring 13, whose other supporting surface consists of the inner side of rear wall 11 of jet 7. A ring 24 is formed in the lower region of core piece 12 and six projections 23 with triangular profiles are formed in its upper region. Ring 24 serves, together with the undercutting of hollow cylinder 19, as a lateral guide for coil spring 13 and to delimit the travel when insert 10 is depressed, while the six projections 23 are installed and shaped such that they engage with an exact a fit as possible when insert 10 is pressed down into these grooves 18. In this manner, all the output openings can be freed of contaminants or calcium deposits by a single downward push of the insert into the so-called cleaning position (FIG. 2, right). A narrow lateral guide of insert 10 in groove 20 of side wall 21 ensures that projections 23 and the triangular grooves are aligned with each other.

Figure 4:
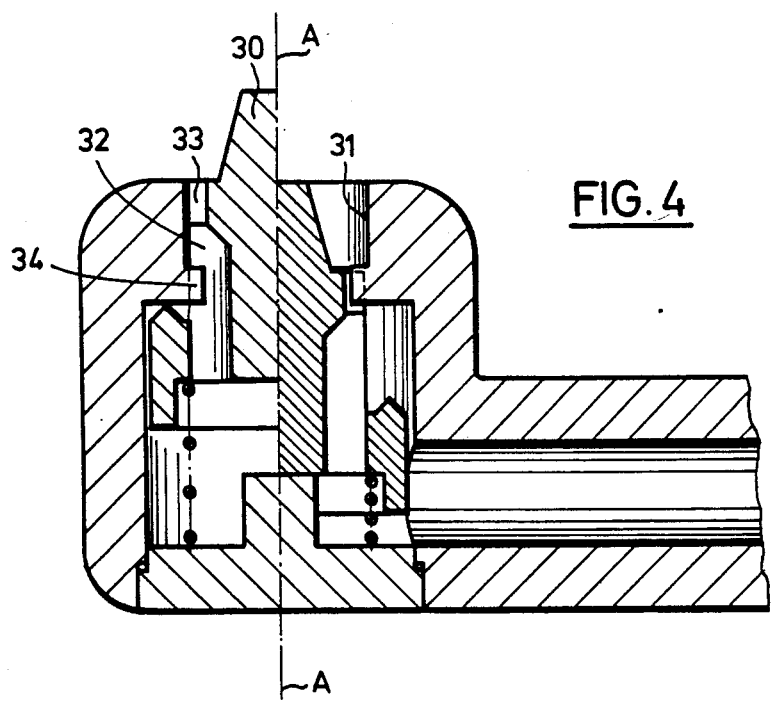
FIG. 4 is a lengthwise section through a second embodiment of a multiple-stream jet, whereby the insert is again in the spray position in the left part of the figure while it is shown in the cleaning position in the right part of the figure.

FIG. 4 shows a second embodiment of a jet wherein an insert 30 is shown, once again in the left part of the figure, in the spraying position while the insert is in the cleaning position in the right part of this Figure. The outlet openings are formed by the outer limit 31 of opening 32 and by the grooves 33 provided in insert 30. In this embodiment, another six (for example) projections 34 are formed on the inner jacket surface of cylindrical jet 7 which forms the outer limit 31 of opening 32, which projections engage grooves 33 when insert 30 is depressed in the manner described for the first embodiment. Insert 30 is again provided with a guide to prevent rotation about its axis A, which guide can correspond to the guide in the description of FIG. 3.

Of course, the first-described embodiment can also be used in a jet which has only one preferably centered outlet opening to dispense a single stream of liquid. In this case, the upper end of core piece 12 is tapered to such a degree that, when insert 10 is depressed, it can engage the single outlet opening directly, which opening is arranged for example centrally in insert 10, and can thus remove contaminants or calcium deposits. In addition, a corresponding cleaning device can also be produced in a combination jet. This will be shown in greater detail below in another embodiment.

According to FIGS. 5, 6, and 7, jet 107 again consists essentially of a cylindrical liquid chamber 108, which is supplied through a supply line 109 traversing shaft 105 and a vertically displaceable core piece 111 in an opening 110 formed in the upper side of liquid chamber 108. Liquid chamber 108 formed from a circular side wall 127 is limited at its lower side by an insert 115, on which a centering piece 116 is formed which projects into the interior of liquid chamber 108, said centering piece having two rectangular grooves 117 and tapering above the two grooves 117 into a small-diameter cylinder 118. Core piece 111 has a bore 113 terminating in an outlet opening 112, in which bore centering piece 116 engages, which provides core piece 111 with guidance during a vertical movement.

By means of a coil spring 114, which abuts insert 115 on the one hand and core piece 111 in a circular groove 119 from the bottom on the other hand, core piece 111 is pretensioned sufficiently to press a bevel 120 formed on core piece 111 so firmly against a rounded lower edge 121 of the limit of opening 110 that no water can pass between the limit of opening 110 and the contour of core piece 111.

According to FIG. 5, left, in which core piece 111 is in its upper position, because of the above-mentioned seal between opening 110 and core piece 111, only liquid from outlet opening 112 can be emitted, i.e. jet 107 emits a single stream. Hence, the liquid entering via incoming line 109 flows around centering piece 116 and rises in the two rectangular grooves 117 into bore 113 and finally arrives at outlet opening 112.

If core piece 111 is pressed downward against the force exerted by coil spring 114, it locks into the position shown in FIG. 2 on the right. The device providing this locking action will be described in more detail below in connection with the explanation of FIG. 8. When core piece 111 is depressed, cylindrical upper end 118 penetrates outlet opening 112 and removes any contaminations or calcium deposits therefrom.

In its lower position of core piece 111, the lower part of centering piece 116 seals off bore 113 of core piece 111, and hence outlet opening 112 from liquid chamber 108. At the same time, however, six semicircular outlet openings 122 are exposed, which openings are formed by the contour of core piece 111 and by six recesses 135 provided in the edge of opening 110 (FIG. 7) and which in the upper position of core piece 111 are largely closed on the one hand by bevel 120 and the rounded lower edge 121 of the edge of opening 110 and on the other hand by semicylindrical noses 123 formed on core piece 111. Thus the liquid flowing from liquid chamber 108 only flows out of the six outlet openings 122 when core piece 111 is in the position shown in FIG. 5, right. Jet 107 then acts as a multiple-stream jet.

Every time core piece 111 passes from the lower to the upper position, outlet openings 122 are freed of any contaminants or calcium deposits by the noses 123 engaging them (see also embodiments according to FIGS. 2 and 3).

It can be seen from FIGS. 5 and 7 on the one hand and FIG. 8 on the other hand that locking of movable core piece 111 in its upper and lower positions takes place by a so-called cardioid control. A rib 124 is formed on insert 115, in which rib two recesses 126 and 129 are cut out such that a nose 125 remains between them. Core piece 111 has a projection 128 on the one hand and a notch on the other hand, into which the upwardly bent end 130 of coil spring 114 engages. The downwardly bent end 131 of coil spring 114 is mounted in a nose 132 formed on insert 115.

FIG. 6 shows core piece 111 in its upper position, in which projection 128 is above nose 125. In this position, bevel 120 of core piece 111 is pressed firmly against rounded lower edge 121 of the edge of opening 110 by a pretensioning of coil spring 114. If core piece 111 is depressed, its projection 128 is guided in recess 126 until the lower tip of projection 128 strikes a projection 133 of recess 126. If core piece 111 is then released, the upper tip of projection 128 locks into a corresponding notch 134 of nose 125, whereby core piece 111 is locked into its lower position.

By contrast to the position marked I in FIG. 8 in the position marked II core piece 111 is considerably rotated about its own axis in the direction of the arrow marked A in FIG. 6. Because of this, the coil spring exerts a torsional force acting against the direction of arrow A, which force causes projection 128 to assume the position marked III when projection 128 is depressed again, and finally projection 128 returns to the position marked I when core piece 111 is released.

I claim:

1. Jet tip mounted on the handle of an oral hygiene appliance, with a jet from which a single or multiple stream can be delivered optionally for oral and dental hygiene, said jet tip comprising structure defining a chamber, a first opening in said chamber defining an entrance passage and a second opening in said chamber defining a discharge passage, a core piece disposed in said chamber, said core piece being displaceable between two extreme positions, said core piece exposing in its first extreme position only outlet openings for a multiple stream and in its second extreme position only one exit opening for a single stream, emerging in the stream cross section of the multiple stream, the path of the fluid supplied to said chamber through said first opening remaining unchanged when said core piece is displaced.

2. Jet according to claim 1 and further including a biasing spring, said core piece being on the one hand, automatically locked in one of the two extreme positions by the mechanical tension exerted by said spring and, on the other hand, with any sufficiently great displacement, moving into the other extreme position against the tension exerted by said spring and being likewise automatically locked in said other extreme position.

3. Jet according to claim 2 and further including a projection of said core piece guided through a cardioid control for locking said core piece in said other extreme position.

4. Jet according to claim 3 wherein said spring, in addition to compressive or tensile force, also exerts a tension in another direction, for example a torsional tension, on said core piece for moving said core piece from one extreme position to the other each time it is depressed.

5. Jet according to claim 1 wherein said core piece has a bore terminating in said exit opening for said single stream.

6. Jet according to claim 5 and further including centering piece structure projecting into the interior of said chamber and provided with at least one groove, said centering piece serving as a guide for the bore of said core piece and in the first extreme position of said core piece sealing off said bore of said core piece against the influx of liquid, said core piece including a bevel which, in the second extreme position of said core piece, abuts the lower edge of the boundary of second opening in sealing fashion.

7. Jet according to claim 6 wherein said centering piece includes a cylindrical upper end which engages said exist opening for said single stream to remove contaminants or calcium deposits during the transition of said core piece from the second to the first extreme position, freeing said exit opening of deposits or contaminants thereby.

8. Jet according to claim 1 wherein said core piece is guided positively in said second opening, and said outlet openings for said multiple stream are formed by recesses in said second opening and by the contour of said core piece.

9. Jet according to claim 8 wherein said core piece further includes noses along its contour, said noses being so shaped that, as a result of their motion within said recesses, said outlet openings for the multiple stream are freed of deposits and contamination.

10. Jet tip with jet on the handle of an oral hygiene appliance, from which a multiple stream can be delivered for oral and dental hygiene, jet said jet tip comprising structure defining a chamber, a first opening in said chamber defining an entrance passage and a second opening in said chamber defining a discharge passage, an insert displaceable between a spraying and resting position disposed in said chamber, outlet openings for the multiple stream being formed between said insert and said second opening by grooves, said insert being held in spraying position by spring force, and projections being provided in a surface defining the outlet for said multiple openings, said projections, when said insert is displaced against the action of spring force, engaging said grooves to remove contamination or calcium deposits.

11. Jet according to claim 10 wherein said second opening includes structure which serves as a guide for said insert during displacement.

12. Jet according to claim 10, wherein said chamber defining structure includes centering structure that extends into said second opening, said centering structure serving as a guide during displacement of said insert.

13. Jet according to claim 12 wherein said insert has a bore of circular cross section.

14. Jet according to claim 10 wherein said second opening has a circular cross section.

15. Jet according to claim 10 wherein said spring tension is generated by a coil spring provided between the under side of said insert and the rear wall of said chamber.

16. Jet according to claim 10 wherein said insert is provided with a groove that cooperates with a nose formed in said chamber defining structure for guiding axial movement of said insert.

* * * * *